(12) United States Patent
Rys

(10) Patent No.: US 8,386,051 B2
(45) Date of Patent: Feb. 26, 2013

(54) DISABLING AN IMPLANTABLE MEDICAL DEVICE

(75) Inventor: Kenneth D. Rys, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 124 days.

(21) Appl. No.: 12/982,564

(22) Filed: Dec. 30, 2010

(65) Prior Publication Data

US 2012/0172941 A1 Jul. 5, 2012

(51) Int. Cl.
*A61N 1/00* (2006.01)
(52) U.S. Cl. .......................................................... 607/63
(58) Field of Classification Search ...................... 607/63
See application file for complete search history.

(56) References Cited

U.S. PATENT DOCUMENTS

| | | | |
|---|---|---|---|
| 3,777,762 A | 12/1973 | Nielsen | |
| 3,805,796 A | 4/1974 | Terry, Jr. et al. | |
| 3,945,387 A * | 3/1976 | Adams | 607/31 |
| 5,309,096 A | 5/1994 | Hoegnelid | |
| 5,350,407 A * | 9/1994 | McClure et al. | 607/16 |
| 5,522,856 A | 6/1996 | Reineman | |
| 5,814,089 A * | 9/1998 | Stokes et al. | 607/32 |
| H1765 H | 12/1998 | O'Phelan et al. | |
| 6,358,281 B1 * | 3/2002 | Berrang et al. | 623/10 |
| 6,402,689 B1 * | 6/2002 | Scarantino et al. | 600/300 |
| 6,516,227 B1 | 2/2003 | Meadows et al. | |
| 6,648,914 B2 | 11/2003 | Berrang et al. | |
| 7,694,809 B2 | 4/2010 | Garbini et al. | |
| 2003/0050676 A1 | 3/2003 | Hubelbank et al. | |
| 2005/0277999 A1 | 12/2005 | Strother et al. | |
| 2006/0136012 A1 * | 6/2006 | Koshiol et al. | 607/59 |
| 2006/0190060 A1 | 8/2006 | Greeninger et al. | |
| 2007/0185551 A1 | 8/2007 | Meadows et al. | |
| 2009/0228077 A1 | 9/2009 | Ginggen et al. | |
| 2010/0076516 A1 | 3/2010 | Padiy et al. | |
| 2010/0114248 A1 | 5/2010 | Donofrio et al. | |
| 2010/0142738 A1 * | 6/2010 | Zhang et al. | 381/315 |
| 2010/0268304 A1 * | 10/2010 | Matos | 607/60 |
| 2010/0331914 A1 | 12/2010 | Hill et al. | |
| 2010/0331915 A1 | 12/2010 | Hill et al. | |
| 2011/0276101 A1 * | 11/2011 | Lee et al. | 607/2 |
| 2012/0007441 A1 * | 1/2012 | John | 307/104 |

FOREIGN PATENT DOCUMENTS

| | | |
|---|---|---|
| EP | 1779869 A1 | 5/2007 |
| WO | 2010040189 A1 | 4/2010 |

OTHER PUBLICATIONS

International Search Report and Written Opinion of international application No. PCT/US2011/034630, dated Jul. 18, 2011, 14 pp.

* cited by examiner

*Primary Examiner* — George Manuel
*Assistant Examiner* — Robert N Wieland
(74) *Attorney, Agent, or Firm* — Stephen W. Bauer; Michael J. Ostrom

(57) ABSTRACT

Various techniques for using a disconnection element to disable an implantable medical device (IMD) are described. The disconnection element may be responsive to energy delivered from outside of the IMD to the disconnection element within the IMD. In response to the delivery of the energy, the power source and operational circuitry of the IMD may be decoupled.

20 Claims, 6 Drawing Sheets

DISABLING AN IMPLANTABLE MEDICAL DEVICE

TECHNICAL FIELD

The disclosure relates to implantable medical devices, and, more particularly, to disabling implantable medical devices.

BACKGROUND

A wide variety of medical devices for delivering a therapy or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient.

Implantable cardiac pacemakers or cardioverter-defibrillators, for example, provide therapeutic electrical signals to the heart, e.g., via electrodes carried by one or more implantable medical leads. The therapeutic electrical signals may include pulses for pacing, or shocks for cardioversion or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

Leadless implantable medical devices may also be used to deliver therapy to a patient, and/or sense physiological parameters of a patient. In some examples, a leadless implantable medical device may include one or more electrodes on its outer housing to deliver therapeutic electrical signals to patient, and/or sense intrinsic electrical signals of patient. For example, a leadless cardiac device, e.g., pacemaker, may be used to sense intrinsic depolarizations or other physiological parameters of the heart, and/or deliver therapeutic electrical signals to the heart. Leadless cardiac devices may be positioned within or outside of the heart and, in some examples, may be anchored to a wall of the heart via a fixation mechanism.

SUMMARY

In general, this disclosure describes a disconnection element that may be used to disable an implantable medical device (IMD), such as a leadless pacemaker. For example, the disconnection element may allow a user to disable an IMD by decoupling the power source and operational circuitry of the IMD. The disconnection element may be responsive to energy delivered from outside of the IMD to the disconnection element within the IMD. In response to the delivery of the energy, the power source and operational circuitry of the IMD may be decoupled.

If a power source of an IMD becomes depleted, or if a communication module of the IMD becomes unresponsive to external communication, a disconnection element may be modified to disable the IMD. The ability to disable an IMD using a disconnection element may be particularly advantageous in situations in which communication with the implantable medical device is no longer available or reliable. The ability to disable an IMD using a disconnection element may also be particularly advantageous in situations in which the IMD is relatively difficult to explant, such as when a leadless cardiac device is implanted on or within the heart.

In one example, the disclosure is directed to an implantable medical device comprising a housing configured for implantation within a patient, a power source within the housing, operational circuitry within the housing that receives operational power from the power source and is configured to at least one of monitor the patient or deliver a therapy to the patient, and a disconnection element within the housing and electrically coupled to both the power source and the operational circuitry, wherein the disconnection element is configured to decouple the power source and operational circuitry in response to reception of external energy from outside of the housing.

In another example, an implantable medical device comprises a housing configured for implantation within a patient, at least one of means for monitoring the patient or means for delivering a therapy to the patient within the housing, and means for providing power to the at least one of the means for monitoring or means for delivering within the housing. The implantable medical device further comprises means within the housing for decoupling the means for providing power from the at least one of the means for monitoring or means for delivering in response to reception of external energy from outside of the housing, wherein the means for decoupling is electrically coupled to both the means for providing power and the at least one of the means for monitoring or means for delivering.

In another example, a system comprises a source configured to deliver energy, and an implantable medical device. The implantable medical device comprises a housing configured for implantation within a patient, a power source within the housing, operational circuitry within the housing that receives operational power from the power source and is configured to at least one of monitor the patient or deliver a therapy to the patient, and a disconnection element within the housing and electrically coupled to both the power source and the operational circuitry, wherein the disconnection element is configured to decouple the power source and operational circuitry in response to reception of energy from the source outside of the housing.

In another example, the disclosure is directed to a method comprising attempting to communicate with an implantable medical device via an external programmer, identifying failure of the communication with the implantable medical device, delivering energy to the implantable medical device, the energy configured to modify a disconnection element within the implantable medical device, the disconnection element electrically coupled to both a power source and operational circuitry within the implantable medical device, wherein modification of the disconnection element by the delivered energy decouples the power source and operational circuitry.

The details of one or more examples are set forth in the accompanying drawings and the description below. Other features, objects, and advantages will be apparent from the description and drawings, and from the claims.

DETAILED DESCRIPTION

Figure 1A:
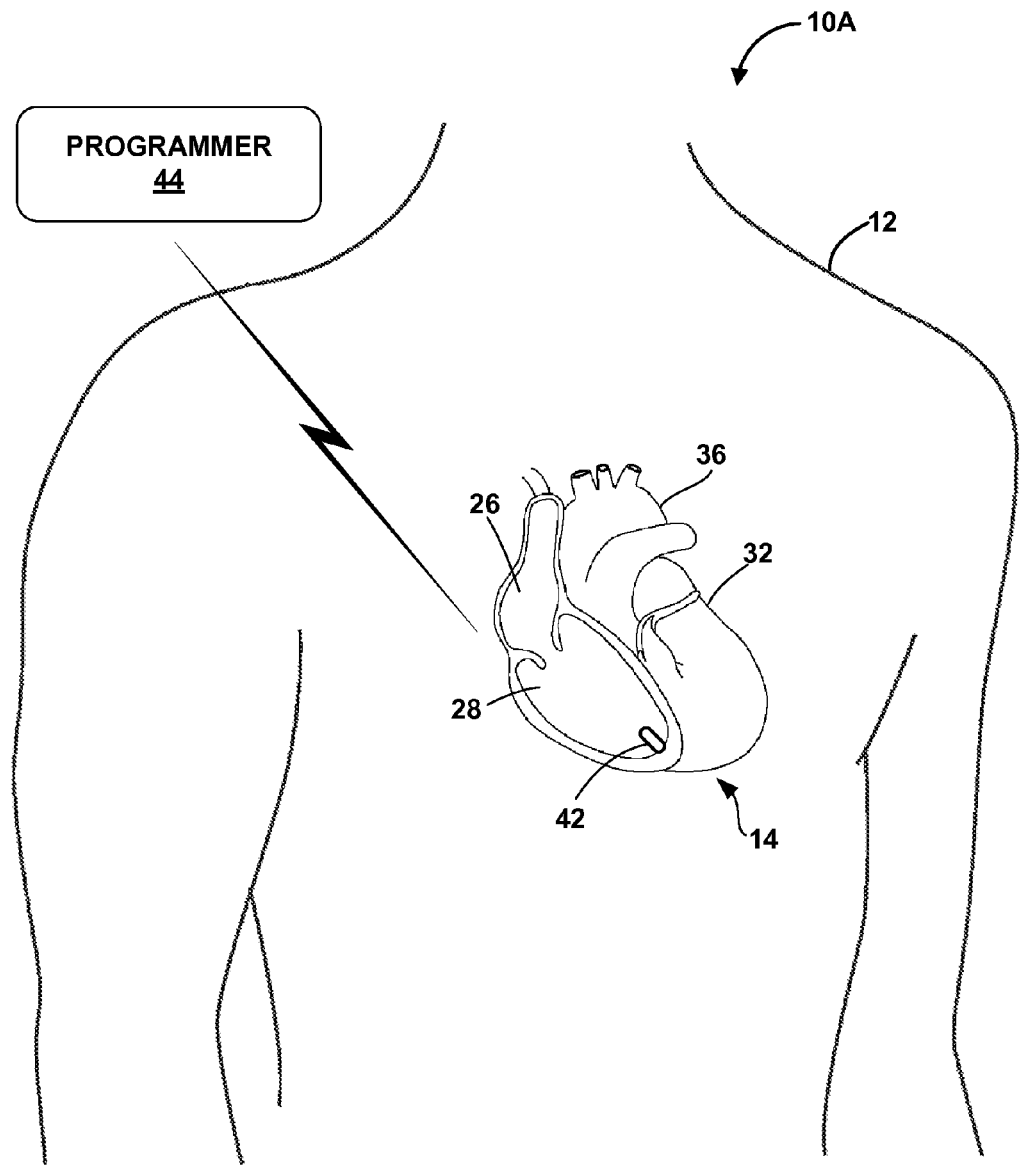
FIG. 1A is a conceptual diagram illustrating an example disconnection system comprising a leadless implantable medical device (IMD) and an external energy source that may be used to modify the disconnection element inside the IMD.

As power sources in IMDs with leads become depleted, typically they are explanted. For example, a pacemaker with leads implanted in the heart of the patient has a separate enclosure that is attached to the proximal end of the leads. This enclosure is often located near the skin of the patient, and can be accessed with minimally invasive procedures. If the power source of an IMD has reached its end of life, or if the IMD is otherwise malfunctioning, the IMD can be replaced with a new IMD by detaching the proximal end of the leads and removing the old IMD.

Once an IMD has reached its end of life, it may be desirable to disable the IMD, e.g., before it is explanted. This may be desired in order to ensure that the IMD does not begin to act erratically due to the unpredictable effects of a depleted power source on a processor in the IMD. For example, without the correct voltage or current, a processor may be unable to correctly detect when a patient needs therapeutic electrical stimulation.

A pacemaker, for example, may fail to detect an abnormal rhythm, and subsequently fail to send the appropriate stimulation signal to return the heart to a normal rhythm. Likewise, the pacemaker may falsely detect an abnormal rhythm, and administer unnecessary stimulation to the patient's heart. Finally, a pacemaker may correctly identify an abnormal rhythm, but then incorrectly calculate the appropriate stimulation in response to the abnormal rhythm, potentially exacerbating the abnormality.

Additionally, after battery depletion or at the end of reliable service, IMDs that deliver therapy, as well as IMDs that do not deliver therapy, such as an implantable sensor or patient monitoring device, may still continue to output communication signals. These communication signals may interfere with other devices, such as communication between another IMD and an external programmer. Accordingly, it may be desirable to disable IMDs that deliver therapy, as well as IMDs that do not deliver therapy, in certain circumstances.

To avoid these problems, IMDs may include software to disable the device after a communication module in the IMD receives an external "disable" command. If the communication module fails though, the "disable" command would not be received and relayed to the software and the pacemaker would fail to shut down. The IMD would then continue to operate, potentially erratically, until the power source was depleted.

Leadless pacemakers are generally designed to be permanently implanted in a patient's heart. They generally are not intended to be removed, and would require a relatively invasive surgery to do so. Advances in the miniaturization of power sources and operational circuitry are such that once a leadless pacemaker reaches end of life, a new leadless pacemaker may be implanted to replace it, without explanting the original pacemaker.

If a communication module in a leadless pacemaker fails, and it is unable to receive a "disable" command, the pacemaker would continue to run until the power source was depleted. As previously noted, erratic or undesired behavior can ensue if a power source becomes too depleted. An invasive surgery would have to be performed to remove the leadless pacemaker.

In general, this disclosure describes a disconnection element that may be used to disable an IMD, such as a leadless pacemaker. If a communications module malfunctions, a user could deliver energy from an external device to a transducer in the leadless pacemaker. Receipt of the energy by the transducer would modify the disconnection element. Once the disconnection element is modified, the power source of a leadless pacemaker is decoupled from the operational circuitry of the leadless pacemaker.

The transducer and associated circuitry within the IMD may be configured to receive energy of a particular type, wavelength, or frequency. An external device may be configured to provide energy configured for receipt by the transducer and configured to modify the disconnection element. In this manner, unintended modification of the disconnection element may be avoided.

As described in more detail below, the disconnection element may be configured in a variety of different ways. In some examples, the disconnection element may be a fuse. In such examples, a transducer would receive the properly configured external energy and overload the fuse, causing it to break, thereby decoupling the power source from the operational circuitry.

FIG. 1A is a conceptual diagram illustrating an example system 10A that may be used to monitor one or more physiological parameters of patient 12 and/or to provide therapy to heart 14 of patient 12. System 10A includes an implantable medical device (IMD) 42, which is capable of being communicatively coupled to programmer 44. IMD 42 may be an implantable leadless pacemaker that provides electrical signals to heart 14 via one or more electrodes (not shown in FIG. 1A) on its outer housing. Additionally or alternatively, IMD 42 may sense electrical signals attendant to the depolarization and repolarization of heart 14 via electrodes on its outer housing. In some examples, IMD 42 provides pacing pulses to heart 14 based on the electrical signals sensed within heart 14.

IMD 42 may also include a disconnection element (not shown in FIG. 1A) within its housing. The disconnection element may be used to disable IMD 42. Patient 12 is ordinarily, but not necessarily, a human patient.

In the example of FIG. 1A, IMD 42 is positioned wholly within heart 14 proximate to an inner wall of right ventricle 28 to provide right ventricular (RV) pacing. Although IMD 42 is shown within heart 14 and proximate to an inner wall of right ventricle 28 in the example of FIG. 1A, IMD 42 may be positioned at any other location outside or within heart 14. For example, IMD 42 may be positioned outside or within right atrium 26, left atrium 36, and/or left ventricle 32, e.g., to provide right atrial, left atrial, and left ventricular pacing, respectively. Depending in the location of implant, IMD 42 may include other stimulation functionalities. For example, IMD 42 may provide atrioventricular nodal stimulation, fat pad stimulation, vagal stimulation, or other types of neurostimulation. In other examples, IMD 42 may be a monitor that senses one or more parameters of heart 14 and may not provide any stimulation functionality. In some examples, system 10A may include a plurality of leadless IMDs 42, e.g., to provide stimulation and/or sensing at a variety of locations.

FIG. 1A further depicts programmer 44 in communication with IMD 42. In some examples, programmer 44 comprises a handheld computing device, computer workstation, or networked computing device. Programmer 44 includes a user interface that presents information to and receives input from a user. It should be noted that the user may also interact with programmer 44 remotely via a networked computing device.

A user, such as a physician, technician, surgeon, electrophysiologist, other clinician, or patient, interacts with programmer 44 to communicate with IMD 42. For example, the user may interact with programmer 44 to retrieve physiological or diagnostic information from IMD 42. A user may also interact with programmer 44 to program IMD 42, e.g., select values for operational parameters of the IMD 42. For example, the user may use programmer 44 to retrieve information from IMD 42 regarding the rhythm of heart 14, trends therein over time, or arrhythmic episodes.

In some examples, the user may use programmer 44 to retrieve information from IMD 42 regarding other sensed physiological parameters of patient 12 or information derived from sensed physiological parameters, such intracardiac or intravascular pressure, activity, posture, respiration, tissue perfusion, heart sounds, or a cardiac electrogram (EGM). In some examples, the user may interact with programmer 44 to program, e.g., select parameters for, therapies and sensing provided by IMD 42.

IMD 42 and programmer 44 may communicate via wireless communication using any techniques known in the art. Examples of communication techniques may include, for example, low frequency or radiofrequency (RF) telemetry, but other techniques are also contemplated.

In addition to communicating with the telemetry module in IMD 42, programmer 44 may be used to modify disconnection element 64 (not shown in FIG. 1A) in IMD 42. In particular, programmer 44 may be configured to deliver energy to IMD 42 to modify the disconnection element within the IMD. In some examples, the energy delivered to modify the disconnection element comprises electrical energy, e.g., a current or voltage. In other examples, the energy delivered to modify the disconnection element comprises an electromagnetic (EM) field, e.g., a radio-frequency (RF) field. In other examples, the energy is light in the visible or near-visible spectrum, or sound waves.

Although a programmer is described herein as the primary example of a device that delivers energy to an IMD to modify a disconnection element, other examples are contemplated. For example, devices that are not configured to program an IMD, or devices that are not otherwise configured to communicate with an IMD, may be configured to deliver energy to an IMD to modify the disconnection element. In general, any external device may be configured to act as an external source of energy that modifies the disconnection element.

In one example, an external defibrillator may be configured to apply electrical energy, e.g., a current or voltage, to the patient in which the IMD is implanted to modify the disconnection element. The electrical energy may be conducted to the IMD through the patient via electrodes (e.g., electrode pads) coupled to the external defibrillator. The electrical energy conducted through the patient to an IMD may be configured to modify the disconnection element, e.g., may have a prescribed frequency, without affecting the patient, e.g., based on the magnitude, frequency or duration of the signal.

Figure 1B:
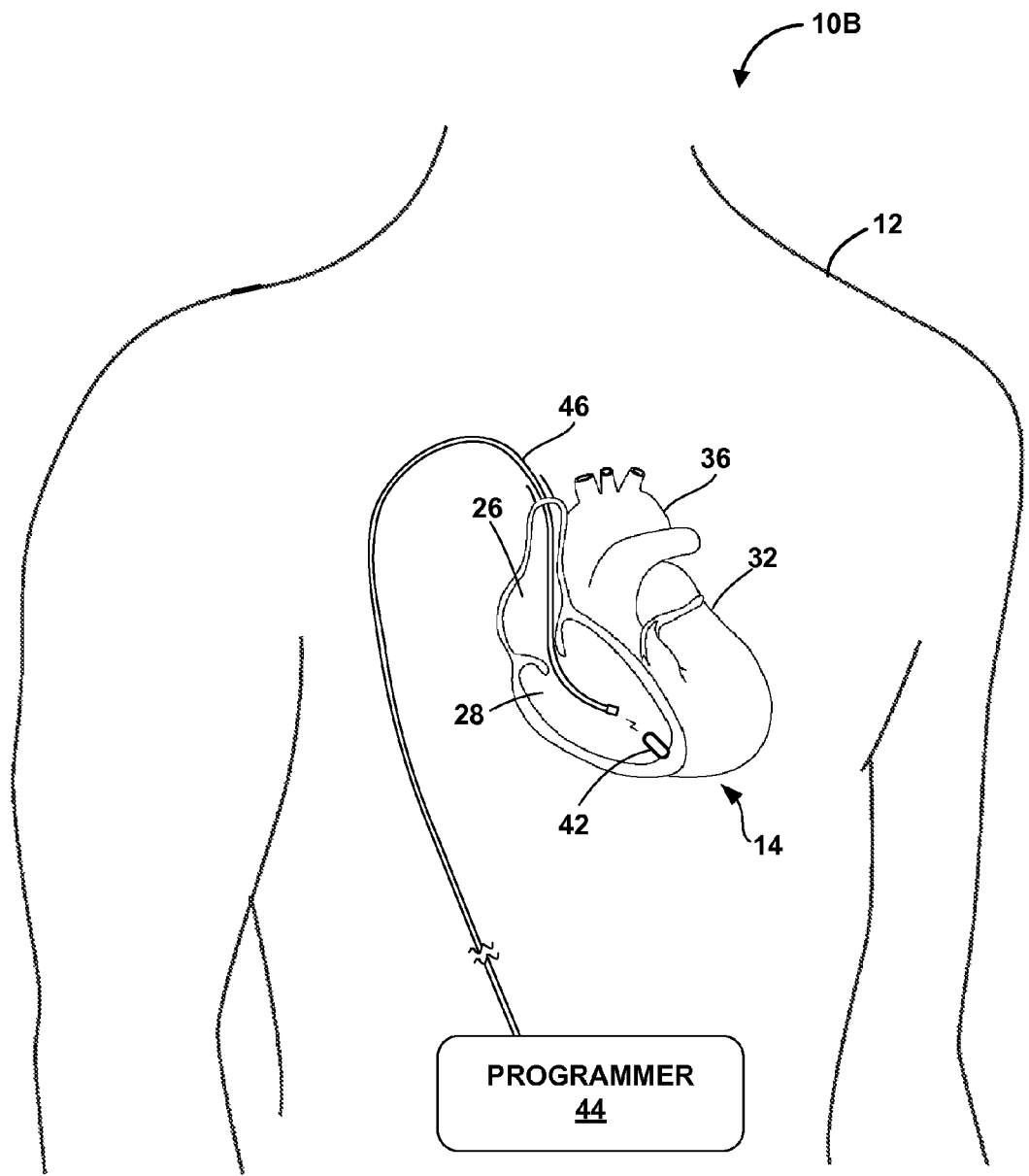
FIG. 1B is a conceptual diagram illustrating another example disconnection system comprising a leadless IMD and an elongated energy delivery element connected to an external energy source that may be used to modify the disconnection element in the IMD.

FIG. 1B is a conceptual diagram illustrating an example system 10B that may be used to monitor one or more physiological parameters of patient 12, and/or to provide therapy to heart 14 of patient 12. Therapy system 10B includes IMD 42, which is coupled to programmer 44, and includes a disconnection element 64 (not shown in FIG. 1B). In one example, IMD 42 may be an implantable pacemaker that provides electrical signals to heart 14 via electrodes on IMD 42. In addition to or as an alternative to pacing therapy, IMD 42 may deliver neurostimulation signals. In other examples, IMD 42 may not provide any stimulation functionalities and, instead, may be a dedicated monitoring device.

As described above with respect to IMD 42 of FIG. 1A, programmer 44 may be used to communicate with IMD 42, as well as to send external energy to the disconnection element in IMD 42 in order to disable IMD 42. In the example of FIG. 1B, programmer 44 is connected to an elongated member 46. Programmer 44 is configured to deliver the energy to IMD 42 via elongated member 46.

In particular, a proximal end of elongated member 46 is connected to programmer 44. A distal end of elongated member 46 may be positioned proximate to IMD 42. Energy may be delivered from the distal end of elongated member 46 to IMD 42. The energy may be conducted from programmer 44 to the distal end of the elongated member, or the distal end of the elongated member may include one or more elements for generation of the energy. In the illustrated example, the distal end of elongated member 46 is directed into heart 14 proximate to IMD 42, e.g., via venous access. In other examples, the distal end of elongated member 46 may be located outside of heart, e.g., via percutaneous or laproscopic access, or outside of patient.

Although the techniques described herein are primarily described with respect to the example of a leadless pacemaker, a disconnection element may be incorporated into any IMD. For example, a disconnection element may be incorporated into IMDs coupled to leads. As another example, a disconnection element may be incorporated into IMDs that do not provide cardiac pacing, cardiac monitoring, or any stimulation. As examples, a disconnection element may be incorporated into an implantable neurostimulator, implantable sensor or monitor, or an implantable pump.

Figure 2:
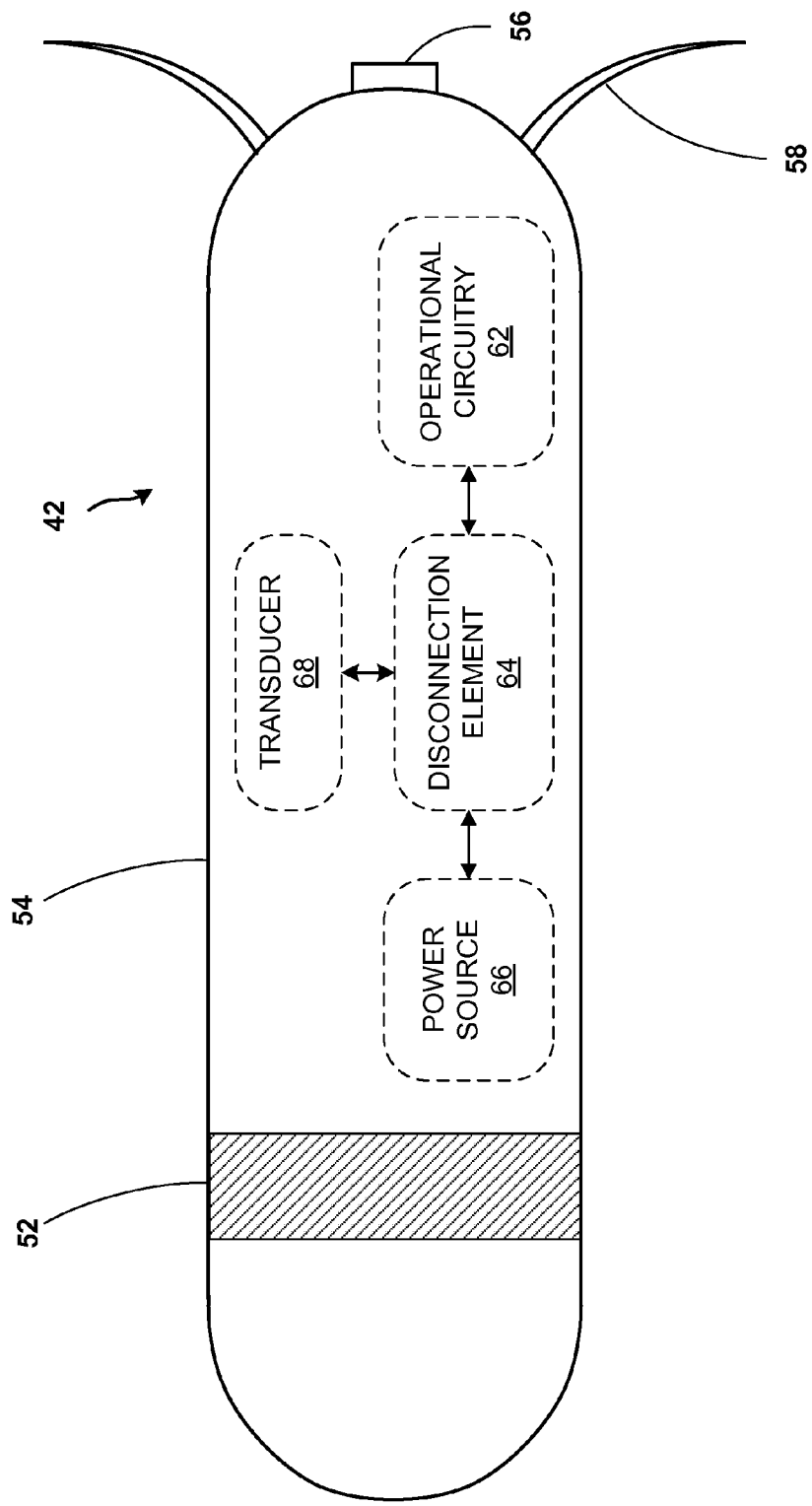
FIG. 2 is a conceptual and functional block diagram illustrating the leadless IMD of FIGS. 1A and 1B in further detail.

FIG. 2 is a conceptual diagram illustrating leadless IMD 42 of FIGS. 1A and 1B in further detail. In the example of FIG. 2, leadless IMD 42 includes fixation mechanism 58. Fixation mechanism 58 may anchor leadless IMD 42 to a wall of heart 14. For example, fixation mechanism 58 may take the form of a plurality of tines. Alternatively, other structures of fixation mechanism 58, e.g., a helical structure that may be screwed into a wall of heart 12, may be utilized. In some examples, fixation mechanism 58 is conductive and may be used as an electrode, e.g., to deliver therapeutic electrical signals to heart 14 and/or sense intrinsic depolarizations of heart 14.

Leadless IMD 42 may also include electrodes 52 and 56 on its outer housing 54. Electrodes 52 and 56 may be used to deliver therapeutic electrical signals to heart 14 and/or sense intrinsic depolarizations of heart 14. Electrodes 52 and 56 may be formed integrally with an outer surface of hermetically-sealed housing 54 of IMD 42 or otherwise coupled to housing 54. In this manner, electrodes 52 and 56 may be referred to as housing electrodes. In some examples, housing electrodes 52 and 56 are defined by uninsulated portions of an outward facing portion of housing 54 of IMD 42. Other division between insulated and uninsulated portions of housing 54 may be employed to define a different number or configuration of housing electrodes. For example, in an alternative configuration, IMD 42 may include a single housing electrode that comprises substantially all of housing 54, and may be used in combination with an electrode formed by fixation mechanism 58 for sensing and/or delivery of therapy.

Leadless IMD 42 may include disconnection element 64 within housing 54, electrically coupled between power source element 66 and operational circuitry 62. In the illustrated example, leadless IMD 42 also includes transducer 68 electrically coupled to disconnection element 64 within housing 54. If a user tries to send a "disable" command to the communication module (not shown in FIG. 2) located within operational circuitry 62, and the communication module does not respond, the user may deliver external energy to transducer 68. Receipt of the energy by transducer 68 will modify disconnection element 64. Thus, in response to the external energy, disconnection element 64 will decouple power source 66 and operational circuitry element 62 in IMD 42. The inclusion of a disconnection element may allow an additional fail-safe for medical devices near end of life. A disconnection element may also provide an additional fail-safe for a medical device that is not at end of life, but in which normal telemetry communications have failed.

Transducer 68 may receive external energy in any of a plurality of forms from programmer 44 (not shown in FIG. 3) or another external energy delivery device. Examples of external energy that may be employed to modify disconnection element 64 include RF fields, light, and sound waves. Examples of transducer 68 may include a coil or other inductive element, a photodiode, or an ultrasonic transducer. In some cases, transducer 68 may at least be partially formed on or through housing 54 of IMD 42. In some examples, housing 54 may be configured to allow the energy to reach transducer 68 within the housing. For example, a portion or all of housing 54 may be transparent or translucent to allow light energy to reach a photodiode or other light transducer 68 within the housing.

In some examples, transducer 68 may be configured to receive energy with a certain configuration, e.g., wavelength or frequency. Transducer 68 may output a current to circuitry including disconnection element 64 in response to receipt of properly configured energy. Disconnection element 64 may be modified to decouple power source 66 from operational circuitry 62 based on the receipt of the current.

For example, transducer 68 may comprise an inductor or coil in which current is induced when exposed to EM, e.g., RF, energy. The inductor or coil may be coupled to a resistor-capacitor (RC) circuit, or resistor-inductor-capacitor (RLC) circuit that is tuned to pass current of a particular frequency, or within a particular band of frequencies, to disconnection element 64. In this manner, energy with a frequency matching the pass band of the RC or RLC circuit will modify disconnection element. Requiring energy of a certain configuration to modify a disconnection element may avoid unintended modification of the disconnection element.

Modification of disconnection element 64 by the energy received from transducer 68 may electrically decouple power source 66 from operational circuitry element 62, disabling IMD 42. In one example, disconnection element 64 may be a fuse configured to break upon receiving current from transducer 68. A fuse may comprise any conductive element configured to break when a prescribed amount of current flows through the conductive element. In another example, disconnection element 64 may be a switch configured to open, e.g., a transistor configured to be off, upon receiving current from transducer 68.

Although described herein with respect to examples that include a transducer to convert the external energy into another form, e.g., current, to modify disconnection element 64, in some examples disconnection element 64 may be directly modified by the external energy. In some examples, the external energy may comprise an electrical signal conducted through the patient to IMD 42. In such examples, the IMD may include electrodes, e.g., electrodes 52 and 56, that are electrically coupled to the disconnection element and receive the electrical energy conducted through the patient. In some examples, the IMD may include an RC or RLC circuit to pass current to the disconnection element when the electrical energy to which the electrodes are exposed has a prescribed frequency.

Furthermore, disconnection element 64 is depicted herein as conceptually being located between operational circuitry 62 and power source 66. However, disconnection element 64 may be physically located anywhere within an IMD 42, and anywhere in relation to operational circuitry 62 and power source 66, so long as modification of the disconnection element 64 prevents power from power source 66 from reaching operational circuitry 62.

Additionally, although in the examples described herein modification of disconnection element 64 prevents power from reaching all operational circuitry 62 of IMD 42, in other examples, modification of disconnection element 64 may only prevent power from reaching a portion of the operational circuitry of an IMD, e.g., some elements and functionality of IMD may remain operational. For example, disconnection element may prevent power from reaching therapy administration module and/or sensor module 88, while allowing processor 80 and/or memory 82 to remain powered and operational.

Figure 3A:
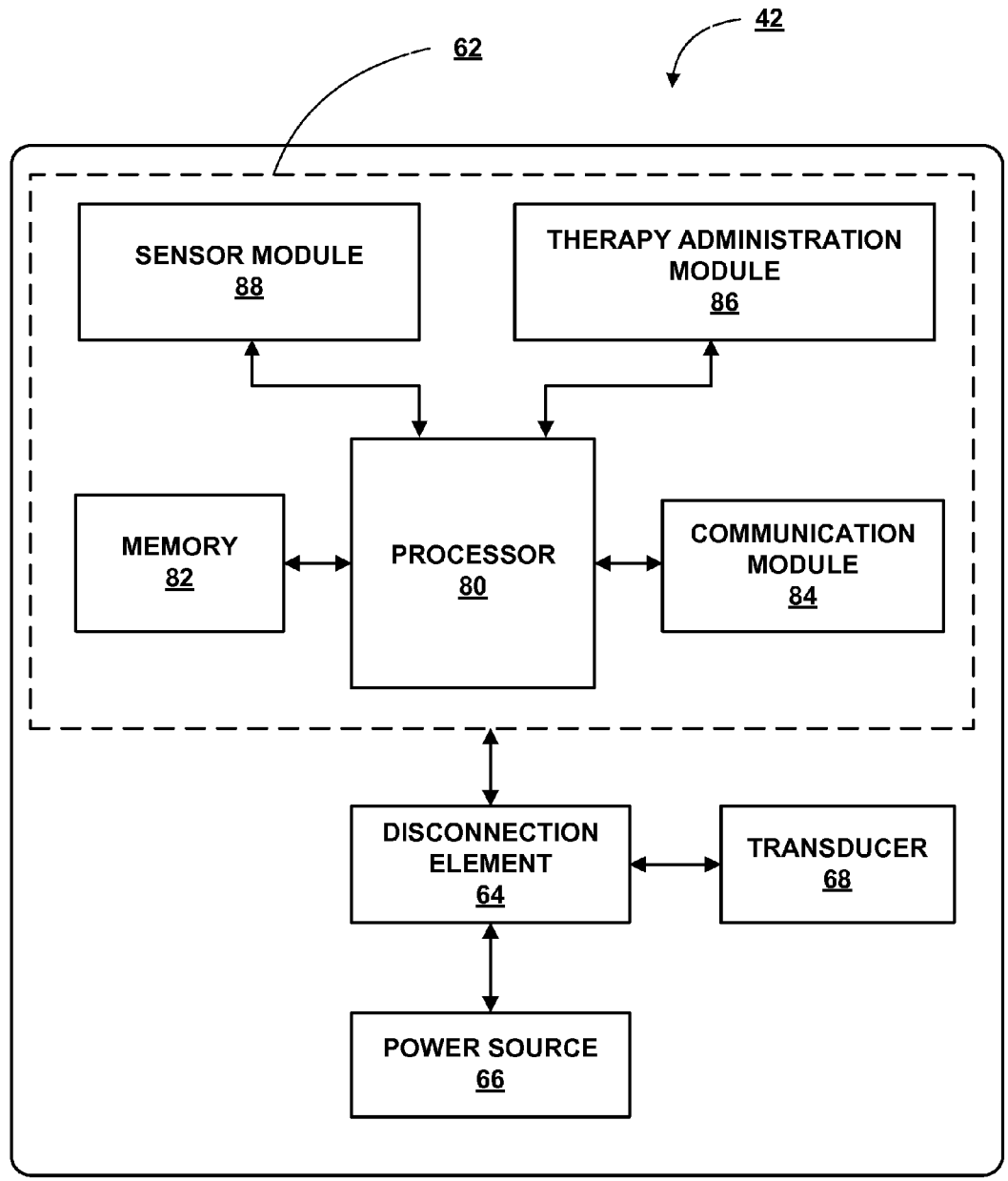
FIG. 3A is a functional block diagram illustrating the example configuration of the IMD in FIG. 2 in further detail.

FIG. 3A is a functional block diagram illustrating one example configuration of IMD 42 of FIG. 2 in further detail. More specifically, FIG. 3 illustrates operational circuitry element 62 of FIG. 2 in further detail. In the example illustrated by FIG. 3, operational circuitry element 62 of IMD 42 includes a processor 80, memory 82, therapy administration module 86, sensing module 88, and communication module 84. As was illustrated in FIG. 2, IMD 42 may include power source 66, transducer 68, and disconnection element 64. Memory 82 may include computer-readable instructions that, when executed by processor 80, cause IMD 42 and processor 80 to perform various functions attributed to IMD 42 and processor 80 herein. Memory 82 may be a computer-readable storage medium, including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof.

Processor 80 controls therapy administration module 86 to deliver stimulation therapy to heart 14 according to operational parameters or programs, which may be stored in memory 82. For example, processor 80 may control therapy administration module 86 to deliver electrical pulses with the amplitudes, pulse widths, frequency, or electrode polarities specified at times by the operational parameters.

Therapy administration module 86, as well as sensor module 88, is electrically coupled to electrodes of IMD 42. In the example of IMD 42 of FIG. 3, therapy administration module 86 and sensor module 88 are coupled to electrodes 56 and 58, e.g., via conductors disposed within housing 54 of IMD 42. In examples in which fixation mechanism 58 functions as an electrode, therapy administration module 86 and sensor module 88 may also be coupled to fixation mechanism 58, e.g., via a conductor disposed within housing 54 of IMD 42.

In the example illustrated in FIG. 3, therapy administration module 86 is configured to generate and deliver electrical stimulation therapy to heart 14. For example, therapy administration module 86 may deliver pacing and/or neurostimulation therapy via at least a subset of the available electrodes. In some examples, therapy administration module 86 delivers one or more of these types of stimulation in the form of electrical pulses. In other examples, therapy administration module 86 may deliver one or more of these types of stimulation in the form of other signals, such as sine waves, square waves, or other substantially continuous time signals. Sensor module 88 monitors signals from at least a subset of the available electrodes in order to monitor electrical activity of heart 14. In some examples, sensor module 88 comprises an amplifier configured to detect either R-waves or P-waves. In some examples, sensor module 88 or processor 80 may include an analog-to-digital converter for digitizing the signal received from a sensing channel for electrogram (EGM) signal processing by processor 80.

During pacing, an escape interval counter maintained by processor 80 may be reset upon sensing of R-waves or P-waves by sensor module 88. Processor 80 may control therapy administration module 86 to deliver a pacing pulse to heart 14 upon expiration of an escape interval. Processor 80 may reset the escape interval counter upon the generation of pacing pulses by therapy administration module 86, or detection of an intrinsic depolarization in a chamber, and thereby control the basic timing of cardiac pacing functions. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect heart rate, such as an atrial rate or ventricular rate.

Telemetry module 84 includes any suitable hardware, firmware, software or any combination thereof for communicating with another device, such as programmer 44 (FIGS. 1A and 1B). Under the control of processor 80, telemetry module 84 may receive downlink telemetry from and send uplink telemetry to programmer 44 with the aid of an antenna, which may be internal and/or external. Processor 80 may provide the data to be uplinked to programmer 44 and receive downlinked data from programmer 44 via an address/data bus. In some examples, telemetry module 84 may provide received data to processor 80 via a multiplexer.

Figure 3B:
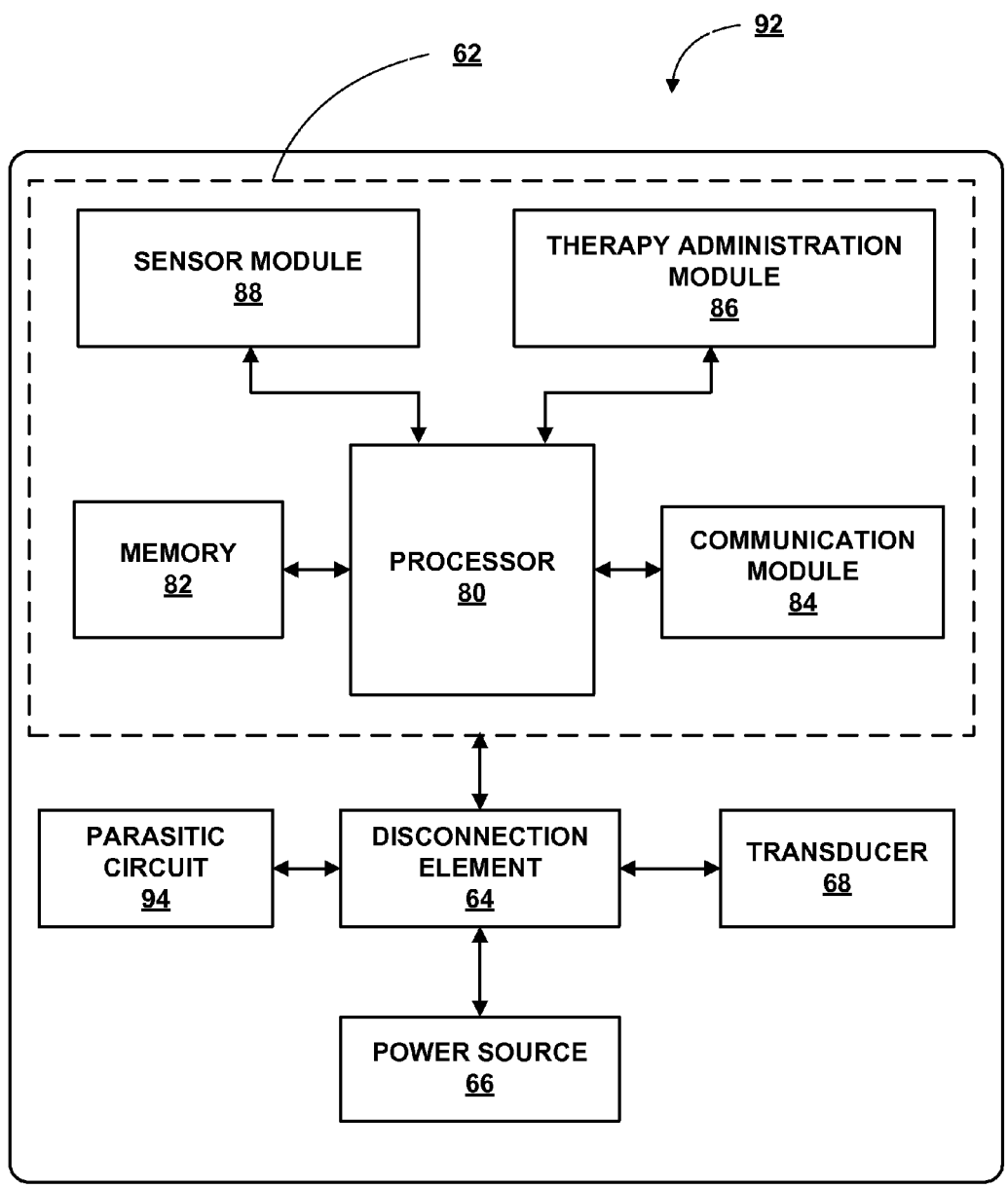
FIG. 3B is a functional block diagram illustrating an example configuration of another IMD.

FIG. 3B is a functional block diagram illustrating another example IMD 92. IMD 92 includes many functional components similar to those of IMD 42 depicted in FIG. 3A, which are giving like numbers in FIG. 3B. Additionally, as illustrated in FIG. 3B, IMD 92 includes a parasitic circuit 94 electrically coupled to power source 66.

As described above, modification of disconnection element 64 electrically disconnects operational circuitry 62 from power source 66. In the example of FIG. 3B, the modification of disconnection element 64 may also connect power source 66 to parasitic circuit 94. In some examples, the modification of disconnection element 64 may switch the connection of power source 66 from operational circuitry 62 to parasitic circuit 94. In such examples, disconnection element 64 may comprise a switch or switch network, such as a transistor or array of transistors.

When connected to power source 66, parasitic circuit 94 may function to drain power from, and completely or substantially completely deplete the power source. Parasitic circuit 94 may comprises a resistor or series of resistors, in some examples.

Figure 4:
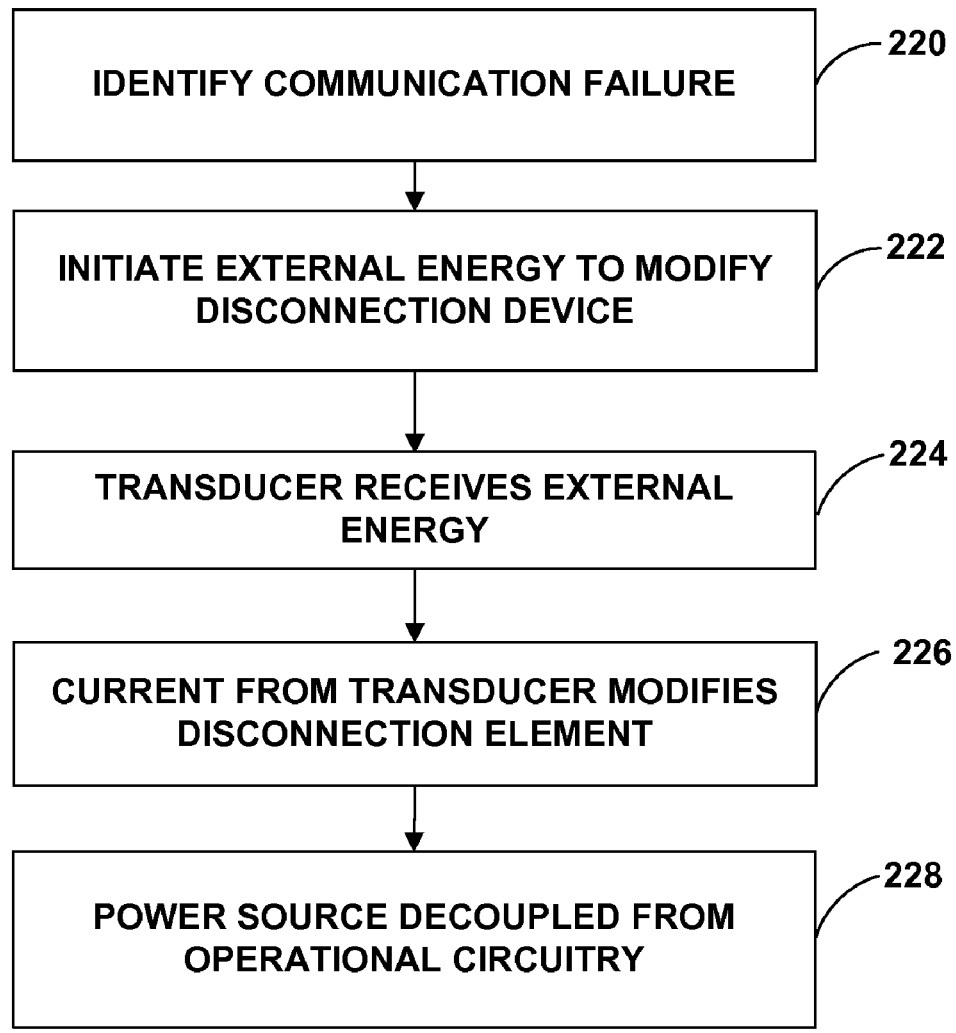
FIG. 4 is a flow diagram of an example method using a disconnection system to disable an IMD.

FIG. 4 is a flow diagram illustrating an example method for disabling a medical device. A user may identify a communication failure between programmer 44 and communication module 84 (220). For example, the user may be trying to disable IMD 42 at its end of life, and communication module 84 may not respond to signals sent from programmer 44, or may respond with erratic or non-standard signals. In response to the communication failure, the user may initiate delivery of external energy from programmer 44 to modify disconnection device 64 (222).

Transducer 68 receives the external energy from programmer 44 (224). The energy may be in any of a variety of forms, including RF energy, light, and sound. Transducer 68 may be configured to convert the external energy into another form of energy, e.g., current. The current from transducer 68 modifies disconnection element 64 (226). The modification of disconnection element 64 electrically decouples power source 66 from operational circuitry 62 (228).

In other examples, as described above, a transducer may not be required to convert the external energy to another form for modifying the disconnection element. For example, the external energy may be in the form of electrical energy of a prescribed frequency conducted through the patient to electrodes 52, 56, or other electrodes, of IMD 42. The electrodes may be coupled to disconnection element 64 via an RC or RLC circuit that is tuned to allow current of the prescribed frequency to reach the disconnection element. Furthermore, in some examples, modification of disconnection element 64 may switch the connection of power source 66 from operational circuitry 62 to parasitic circuit 94, thereby depleting the power source 66.

Various examples have been described. These and other examples are within the scope of the following claims.

The invention claimed is:

1. An implantable medical device, comprising:
    a housing configured for implantation within a patient;
    a power source within the housing;
    operational circuitry within the housing that receives operational power from the power source and is configured to at least one of monitor the patient or deliver a therapy to the patient; and
    a disconnection element within the housing and electrically coupled to both the power source and the operational circuitry, wherein the disconnection element is configured to decouple the power source and operational circuitry in response to reception of external energy from outside of the housing, and wherein the disconnection element comprises a fuse configured to break in response to the reception of the external energy.

2. The implantable medical device of claim 1, wherein the operational circuitry comprises at least one of:

a sensor module that receives a physiological signal of the patient; and
a therapy administration module configured to administer therapy.

3. The implantable medical device of claim 1, wherein the operational circuitry comprises at least one of:
a processor that controls the at least one of the monitoring of the patient or the delivery of the therapy to the patient;
a memory; and
a communication module for communication with an external programmer.

4. The implantable medical device of claim 1, wherein the implantable medical device comprises a leadless pacemaker.

5. The implantable medical device of claim 1, further comprising a plurality of electrodes coupled to the operational circuitry and the disconnection element, wherein operational circuitry is configured to at least one of deliver therapeutic electrical stimulation or sense physiological signals via the electrodes, and wherein the external energy comprises electrical energy received by the electrodes.

6. The implantable medical device of claim 5, wherein the electrodes are coupled to the disconnection element via at least one of a resistor-capacitor circuit or resistor-inductor-capacitor circuit tuned to allow current of a prescribed frequency to pass from the electrodes to the disconnection element.

7. The implantable medical device of claim 1, further comprising a transducer element electrically coupled to the disconnection element and configured to provide a current to the disconnection element as a function of the external energy to modify the disconnection element.

8. The implantable medical device of claim 7, wherein the external energy is an electromagnetic field at one of a plurality of frequencies and the transducer is configured to respond to the frequency of the external energy.

9. The implantable medical device of claim 7, wherein the external energy is sound waves at one of a plurality of frequencies and the transducer is configured to respond to the frequency of the external energy.

10. The implantable medical device of claim 7, wherein the external energy is light at one of a plurality of wavelengths and the transducer is configured to respond to the wavelength of the external energy.

11. The implantable medical device of claim 1, further comprising a parasitic circuit configured to drain the power source, wherein the disconnection element is configured to couple the power source and the parasitic circuit in response to the reception of the external energy from outside of the housing.

12. An implantable medical device, comprising:
a housing configured for implantation within a patient;
at least one of means for monitoring the patient or means for delivering a therapy to the patient within the housing;
means for providing power to the at least one of the means for monitoring or means for delivering within the housing; and
means within the housing for decoupling the means for providing power from the at least one of the means for monitoring or means for delivering in response to reception of external energy from outside of the housing, wherein the means for decoupling is electrically coupled to both the means for providing power and the at least one of the means for monitoring or means for delivering, and wherein the means for decoupling comprises a fuse configured to break in response to the reception of the external energy.

13. A system comprising:
a source configured to deliver energy; and
an implantable medical device comprising:
a housing configured for implantation within a patient;
a power source within the housing;
operational circuitry within the housing that receives operational power from the power source and is configured to at least one of monitor the patient or deliver a therapy to the patient; and
a disconnection element within the housing and electrically coupled to both the power source and the operational circuitry, wherein the disconnection element is configured to decouple the power source and operational circuitry in response to reception of energy from the source outside of the housing, and wherein the disconnection element comprises a fuse configured to break in response to the reception of the external energy.

14. The system of claim 13, wherein the implantable medical device comprises a leadless pacemaker.

15. The system of claim 13, wherein the source comprises a programmer configured to communicate with the implantable medical device.

16. The system of claim 13, wherein the source comprises an external defibrillator.

17. The system of claim 13, wherein the source comprises an elongated element for delivering the energy, the elongated element configured to be guided within the patient to a position proximate to the implantable medical device in order to deliver the external energy.

18. A method comprising:
attempting to communicate with an implantable medical device via an external programmer;
identifying failure of the communication with the implantable medical device; and
delivering energy to the implantable medical device, the energy configured to modify a disconnection element within the implantable medical device, the disconnection element electrically coupled to both a power source and operational circuitry within the implantable medical device, wherein modification of the disconnection element by the delivered energy decouples the power source and operational circuitry, and wherein the disconnection element comprises a fuse configured to break in response to the reception of the delivered energy.

19. The method of claim 18, wherein delivering energy comprises delivering energy from outside of a housing of the implantable medical device.

20. The method of claim 18, wherein delivering energy comprises delivering energy from outside of the patient.

* * * * *